United States Patent [19]
Dubois et al.

[11] Patent Number: 5,654,382
[45] Date of Patent: Aug. 5, 1997

[54] EPOXY RESIN HIGH IN ORTHO BISPHENOL F

[75] Inventors: Robert A. Dubois, Houston, Tex.; Hideyuki Ohnishi, Susono, Japan; Allyson J. Malzman, Lake Jackson, Tex.

[73] Assignee: The Dow Chemical Company, Midland, Mich.

[21] Appl. No.: 497,494

[22] Filed: Jun. 30, 1995

[51] Int. Cl.$^6$ .................. C08G 59/00; C08G 65/08; C08G 65/14
[52] U.S. Cl. .................. 525/523; 528/104; 549/560
[58] Field of Search .................. 528/104; 525/523; 548/560

[56] References Cited

U.S. PATENT DOCUMENTS

| | | | |
|---|---|---|---|
| 3,477,990 | 11/1969 | Dante et al. | 260/47 |
| 3,787,520 | 1/1974 | Labana et al. | 260/836 |
| 4,499,255 | 2/1985 | Wang et al. | 528/95 |
| 4,612,156 | 9/1986 | Heinemeyer et al. | 264/176 R |
| 4,778,863 | 10/1988 | Wang et al. | 525/507 |

FOREIGN PATENT DOCUMENTS

| | | | |
|---|---|---|---|
| 0 369 071 A1 | 5/1990 | European Pat. Off. | |
| 0 684 268 A1 | 11/1995 | European Pat. Off. | |
| 59-8767 | 1/1984 | Japan | C09D 3/58 |
| H2166114 | 6/1990 | Japan | C08D 163/02 |
| H333169 | 2/1991 | Japan | C09D 5/00 |
| H345620 | 2/1991 | Japan | C08G 59/20 |
| H376770 | 4/1991 | Japan | C08G 59/18 |

OTHER PUBLICATIONS

Chemical Abstracts 94:185091, "Thin Layer Chromatography of Dihydroxydiphenylmethane Isomers", Zowall et al. 1980.

Chemical Abstracts 110:158883, "Metal Part with Wear–Resistant Layer and Easy Defect Defection".

Chemical Abstracts 83:148231, "Moderate–Temperature Curable Epoxy for Advanced Composites".

H. Lee et al., *Epoxy Resins*, p. 13 (McGraw Hill Book Company, Inc., 1957).

H. Lee & K. Neville, *Handbook of Epoxy Resins*, at 2–6 to 2–8 (McGraw–Hill Book Co. 1967).

H. Lee & K. Neville, *Handbook of Epoxy Resins*, at 2–9 (McGraw–Hill Book Co. 1967).

H. Lee & K. Neville, *Handbook of Epoxy Resins*, at 2–4 to 2–6 (McGraw–Hill Book Co. 1967).

*Primary Examiner*—Frederick Krass

[57] ABSTRACT

An epoxy resin prepared from a component comprising a bisphenol F having high ortho isomer content is claimed. Ortho isomer content is defined as follows:

$$(A+2B)/2$$

A: content of ortho-para isomer of a bisphenol F
O: content of ortho-ortho isomer of a bisphenol F The epoxy resin of the present invention has lower viscosity (e.g. melt viscosity, solution viscosity) and good physical properties (e.g. flexibility), and suitable for various applications such as coating materials, electrical laminates, adhesives, molding products, encapsulation materials, etc.

19 Claims, No Drawings

EPOXY RESIN HIGH IN ORTHO BISPHENOL F

BACKGROUND OF THE INVENTION

The present invention relates to a novel epoxy resin containing a bisphenol-F.

Bisphenol type epoxy resins are conventionally produced by reacting a compound having at least one epoxy group and a bisphenol. The resins have been used in various application areas such as coatings, laminates, insulation materials, encapsulation and potting of electric/electronic devices, adhesives, construction materials, moldings and composites.

Recently, such epoxy resins have been required to meet higher physical, mechanical and chemical standards because of progress of the various technologies such as electric/electronic devices and coatings. Epoxy resins need improved physical properties such as flexibility and film properties, and improved chemical properties such as curability. Furthermore, epoxy resins need to have lower melt/solution viscosity to enable reduced volatile content and increased solid resin content when dissolved in a solvent.

Generally speaking, when the molecular weight of the epoxy resin is increased, physical properties such as flexibility and impact resistance, and chemical properties such as solvent resistance and corrosion resistance are improved, but the melt and/or solution viscosity of the epoxy resins increases and processability deteriorates.

Some improvement has been realized by incorporating bisphenol-F into the epoxy resin. Bisphenol-F epoxy resins have relatively low viscosity compared with bisphenol-A epoxy resins. For example, epoxy resin compositions based on bisphenol-F epoxy resin are disclosed in Japanese Kokai Patent Publications S[5]59-8767, H2-166114, H3-33169, H3-45620 and H3-76770. However, further improvements in viscosity and/or physical properties would be desirable.

It is an object of the present invention to provide an epoxy resin which has both low viscosity and good physical properties.

SUMMARY OF THE INVENTION

The present invention relates to an epoxy resin which has low viscosity and improved physical properties.

More specifically, the present invention relates to an epoxy or phenoxy resin comprising repeating units derived from a bisphenol-F, wherein at least 46 percent of the hydroxyl groups in the bisphenol-F are in ortho position with respect to the methylene group.

In a preferred embodiment, the epoxy resin of the present invention is prepared by reacting a compound having at least one epoxy group with a bisphenol-F compound wherein at least 46 percent of the hydroxyl groups in the bisphenol F are in ortho position with respect to the methylene group.

A DETAILED DESCRIPTION OF THE INVENTION

Conventional bisphenol-F used as raw material of conventional epoxy resin comprises several isomers. For example, conventional bisphenol-F mainly comprises bis(2-hydroxylphenyl)methane (i.e. ortho-ortho isomer), bis(4-hydroxylphenyl)methane (i.e. para-para isomer) and 4-hydroxylphenyl-2'-hydroxyphenylmethane (i.e. ortho-para isomer). These isomers are illustrated in Formula I (a)–(c):

Formula I

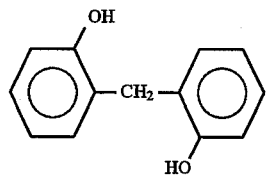

(a) bis(2-hydroxyphenyl)methane

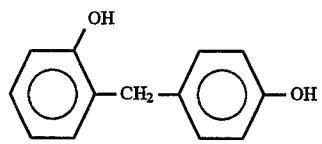

(b) 4-hydroxyphenyl-2'-hydroxyphenylmethane

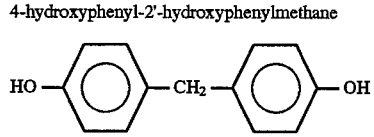

(c) bis(4-hydroxyphenyl)methane

It has been reported that bisphenol F which contains a high concentration of bis(4-hydroxyphenyl)methane (para-para isomer content) provides superior viscosity and physical properties. For example, Japanese Patent Publication H2-166114 discloses that para-para isomer content of bisphenol-F is preferably 33 percent or more when producing bisphenol-F type epoxy resin by reacting a diglycidyl ether of bisphenol-F with bisphenol-F.

However, we have discovered that a higher proportion of ortho-phenol moieties in the bisphenol-F improves the melt/solution viscosity and physical properties of an epoxy resin. In other words, a higher content of bis(2-hydroxyphenyl)methane (ortho-ortho isomer) and 4-hydroxyphenyl-2'-hydroxyphenylmethane (ortho-para isomer) provides an epoxy resin having improved melt/solution viscosity and cured physical properties.

The bis(2-hydroxyphenyl)methane (ortho-ortho isomer) has two hydroxyl groups in ortho position with respect to the methylene group, and the 4-hydroxyphenyl-2'-hydroxyphenylmethane has one hydroxyl group in ortho position with respect to the methylene group. Therefore, the ratio of ortho hydroxyl groups in the bisphenol-F as a percentage of total hydroxyl groups in the bisphenol-F (hereafter ortho hydroxyl group ratio) is approximately defined by equation (1):

$$\text{(ortho hydroxyl group ratio)} = (A + 2B)/2 \quad \ldots \text{equation} \quad (1)$$

wherein:

A is the weight percent of 4-hydroxyphenyl-2'-hydroxyphenylmethane in the bisphenol-F; and B is the weight percent of bis(2-hydroxyphenyl)methane in the bisphenol-F.

In the high ortho bisphenol-F, which is used as one of the raw materials in the present invention, at least about 46.0 percent of the hydroxyl groups are in ortho position with respect to the methylene group. In other words, the high ortho bisphenol-F satisfies the following equation, $$46.0 \leq (A + 2B)/2 \leq 100$$

wherein:

A and B have the meanings previously given.

The ortho hydroxyl group ratio defined by equation (1) of the bisphenol-F used in the present invention is equal to or more than 46.0, preferably equal to or more than about 48.0, more preferably equal to or more than about 50.0, and most preferably at least about 60.0. If the ortho hydroxyl group ratio of the bisphenol-F is below said range, melt/solution viscosity of the epoxy resin therefrom may tend to be insufficiently low, and physical properties of the epoxy resin therefrom such as flexibility and film properties when utilized as coating material are very often deteriorated.

The maximum ortho hydroxyl group ratio is not critical and may be as high as 100. However, due to practical considerations, such as cost and efficiency, the ortho hydroxyl group ratio is preferably no more than about 95, more preferably no more than about 90, and most preferably no more than about 85.

Conventional crude bisphenol-F usually contains a minor portion of multi-functional components (tris-phenols and the like) in addition to the bi-functional component. It is well known that the viscosity and some of the physical properties of an epoxy resin from the bisphenol-F are improved by minimizing the concentration of multi-functional components. We theorize that the multi-functional component degrades these properties by causing branching of the polymer in a chain extension reaction. For example, Japanese Kokai Patent Publication H3-76770 discloses an epoxy resin produced from bisphenol-F having 96 or more weight percent of bi-functional content, and such epoxy resin has low viscosity and has good processability. The epoxy resin of the present invention may employ bisphenol-F having a high bifunctional content. However, even if the multi-functional content is high, an epoxy resin from high ortho bisphenol-F may provide superior physical properties and lower viscosity as compared to an epoxy resin from a bisphenol-F having a low ortho hydroxyl group ratio.

The high ortho bisphenol-F may be prepared by reacting phenol with formaldehyde, and controlling the isomer content by changing reaction conditions to reduce para-para isomer content. Alternatively, the high ortho bisphenol-F may be prepared by removing para-para isomer from crude bisphenol-F through recrystallization or molecular distillation. Alternatively, the high ortho bisphenol-F can be prepared by adding ortho-para isomer and/or ortho-ortho isomer to conventional crude bisphenol-F or bisphenol-F having low (para-para isomer) content. (The ortho-para isomer and/or ortho-ortho isomer can be recovered from crude bisphenol F by recrystallization or molecular distillation.

The high ortho bisphenol-F is used to prepare epoxy resins of the present invention by reaction with other raw materials, which may be any known compounds used in a preparation of a bisphenol-type epoxy resin. Examples of the other raw materials include compounds having one epoxy group, compounds having more than one epoxy group and bisphenols.

The compound having at least one epoxy group is preferably either epihalohydrin or epoxy resin, more preferably either epihalohydrin or an epoxy resin derived from a bisphenol, and most preferably either epichlorohydrin or a liquid diglycidyl ether of a bisphenol.

Epoxy resins of the present invention may be made from high ortho bisphenol-F by conventional processes for making advanced epoxy resins. Generally, two different processes are commonly known and practiced: the taffy process and the advancement process.

In the "taffy process," a moderate molar excess of epihalohydrin is reacted with a bisphenol component. This process is described in numerous references, such as H. Lee & K. Neville, *Handbook of Epoxy Resins*, at 2–6 to 2–8 (McGraw-Hill Book Co. 1967), which is incorporated herein by reference. In the present invention, the bisphenol component contains high ortho bisphenol-F. It may optionally further contain a second bisphenol, such as bisphenol-A, bisphenol-K, bisphenol-S, bisphenol-AD, or halides and mixtures thereof. The bisphenol component preferably contains at least about 10 weight percent high ortho bisphenol-F, more preferably at least about 12 weight percent and most preferably at least about 15 weight percent. The maximum content may be as high as about 100 percent. The molar ratio of epihalohydrin to bisphenol is preferably about 1.1 to about 2.1, and more preferably about 1.2 to about 2.0.

In the "advancement process," a moderate excess of lower molecular weight epoxy resin is reacted with a bisphenol component to make a higher molecular weight epoxy resin. This process is described in numerous references, such as Heinemeyer et al., U.S. Pat. No. 4,612,156 (Sep. 16, 1986) and H. Lee & K. Neville, *Handbook of Epoxy Resins*, at 2–9 (McGraw-Hill Book Co. 1967), which are incorporated herein by reference. In the present invention, either the bisphenol component contains high ortho bisphenol-F, or the lower molecular weight epoxy resin is derived from high ortho bisphenol-F, or both. The lower molecular weight epoxy resin is preferably a liquid epoxy resin. Its epoxy-equivalent weight (EEW) is preferably about 150 to 250, and more preferably about 160 to about 200. The component or components which contain high ortho bisphenol-F may optionally further contain a second compound having more than one phenolic hydroxyl group, such as a bisphenol or a novolac. The compound having more than one phenolic hydroxyl group is preferably a bisphenol, such as bisphenol-A, bisphenol-K, bisphenol-S, bisphenol-AD, or halides and mixtures thereof. The components which contain or are derived from high ortho bisphenol-F preferably contain or are derived from at least about 10 weight percent high ortho bisphenol-F, more preferably at least about 12 weight percent and most preferably at least about 15 weight percent. The maximum content may be as high as about 100 percent.

Lower molecular weight epoxy resins derived from high ortho bisphenol-F can be made by reacting high ortho bisphenol-F with a large excess of epihalohydrin. Such processes are well known in the art and are described in numerous references such as Wang et al., U.S. Pat. No. 4,499,255 (Feb. 12, 1985); Wang et al., U.S. Pat. No. 4,778,863 (Oct. 18, 1988); and H. Lee & K. Neville, *Handbook of Epoxy Resins*, at 2–4 to 2–6 (McGraw-Hill Book Co. 1967), which are incorporated herein by reference.

Even when the high ortho bisphenol-F is used as a mixture with a conventional bisphenol, the advantage of the present invention, such as reduction of the viscosity and improvement in physical properties for epoxy resins therefrom, may be expected. For example, when conventional bisphenol-A is mixed with high ortho bisphenol-F of the present invention, and used as a raw material of epoxy resin by reacting with a component having at least one epoxy group, the advantageous effects such as reduction of the viscosity and improvement in physical properties of epoxy resins therefrom may be expected. Therefore, the high ortho bisphenol-F of the present invention may be used as additive-like material to improve various properties of the epoxy resin therefrom.

The epoxy resins of the present invention are preferably made by reacting conventional low-molecular-weight epoxy resin (LER) and high ortho bisphenol-F, and are more preferably made by reacting conventional bisphenol A type LER and high ortho bisphenol-F. These resins have a good balance of properties such as solubility in organic solvent and production cost.

The conventional LER used in the present invention may be any epoxy resins having relatively low molecular weight, preferably epoxy resins produced by reacting a bisphenol and epihalohydrin, more preferably a bisphenol-A and epichlorohydrin. Examples of such conventional LER may include D.E.R.* 331L and D.E.R.* 383J, which are commercially available from The Dow Chemical Company (*—trademark of The Dow Chemical Company).

A preferred example of the epoxy resin of the present invention may be obtained by reacting an epoxy resin and bisphenol, preferably with a catalyst, at 60° C.–280° C. preferably at 100° C.–200° C. for 30 minutes to 12 hours, preferably for 1 to 6 hours. The catalyst may be any known catalyst such as: an alkali metal hydroxide or alkaline earth metal hydroxide, such as sodium hydroxide and potassium hydroxide; an imidazole, such as 2-methyl imidazole; a tertiary amine, such as triethylamine, tripropylamine and tributylamine; a phosphonium salt, such as ethyltriphenylphosphonium chloride, ethyltriphenylphosphonium bromide, and ethyltriphenylphosphonium acetate; and/or an ammonium salt, such as benzyltrimethylammonium chloride and benzyltrimethylammonium hydroxide. The catalyst is preferably a phosphorous catalyst, and more preferably phosphonium salt such as ethyltriphenylphosphonium acetate.

In the production of the epoxy resin, reaction solvent may be used if desired. Examples of the reaction solvent include ketone such as methylisobutyl ketone and methylethyl ketone; glycol ether such as ethyl cellosolve and butyl cellosolve; and/or amide such as N,N-dimethylacetamide. The reaction solvent is preferably a glycol ether having a high boiling point, and is more preferably ethylcellosolve and/or ethylcarbitol.

The epoxy equivalent weight (EEW) of an epoxy resin of the present invention is preferably at least about 200, more preferably at least about 250, more highly preferably at least about 500, and most preferably at least about 750. (EEW is conveniently measured by titration according to known processes.)

The maximum molecular weight of the epoxy resin is not critical to the present invention, and depends solely upon the intended use of the resin. Resins of the present invention may optionally be phenoxy resins having a weight average molecular weight ($M_w$) up to about 250,000 or higher. If they are intended for use as epoxy resins, then their EEW is preferably no more than about 10,000; more preferably no more than about 5000; and most preferably no more than about 2500. If they are intended for use as phenoxy resins, then their $M_w$ is preferably at least about 10,000, more preferably at least about 50,000 and most preferably at least about 100,000.

The epoxy resin of the present invention may be modified if desired. For example, the epoxy resin of the present invention may be esterified by reacting with phosphoric acid to give a water solubility or water dispersibility, or may be polyamide modified by reacting with polyamide dicarboxylic acid.

The epoxy resin of the present invention may be used to make coating material such as water-borne coating, solvent-borne coating and powder-coating; adhesives; electric laminates; potted or encapsulated electric/electronic devices; insulation materials; materials for construction and composites.

For example, the epoxy resin of the present invention may be used for powder-coating by blending with known additives including hardener, filler and pigment; kneading and mixing with sufficient heat; and grinding to a desired particle size.

Furthermore, the epoxy resin of the present invention may be used as adhesive or constructive material by blending with known additives including curing agent, hardener, filler, pigment, dye, anti-oxidant, solvent, diluent, flow modifier, viscosity modifier and flame retardant. Examples of suitable curing agents include: guanidines such as dicyanamide; acid anhydrides such as hexahydrophthalic acid anhydride; imidazole and derivatives thereof such as 2-methylimidazole; sebacic acid dihydrazide; urea derivatives; polyamides; polyamines and the like. The filler may include, for example; silica powder, talc, calcium dioxide, clay, carbon black and the like.

The epoxy resin of the present invention may be used in paint compositions by blending with necessary additives and solvents. The additives preferably include, for example: dye, pigment, curing agent, hardener, antioxidant and the like. Any known curing agent may be used in this application, but preferred curing agents include resole, novolac, melamine and urea monomers, oligomers and/or resins. The weight ratio of the epoxy resin and the curing agent is preferably 98:2 to 50:50, more preferably 95:5 to 60:40. Any known cure accelerator may be used if desired.

The composition for the paint may be prepared by dissolving the epoxy resin and curing agent into the solvent; such as glycol ether, aromatic hydrocarbon, alcohol or ketone. The solid content is preferably about 10 to 95 percent by weight. It may preferably be painted as 0.5 to 200 μm, more preferably 2 to 50 μm of dry film thickness on various metal materials such as aluminum plate, tin plate, tin free steel plate, steel plate and the like by known method such as spraying, roll-coating and dipping. The formulation may be cured at 60° to 300° C. in 5 seconds to 30 minutes.

EXAMPLES

The following examples are for illustrative purposes only and they should not be taken as limiting the scope of either the specification or the claims. Unless otherwise stated, all percentage and parts are by weight.

In the following examples, an epoxy equivalent weight (EEW) was determined in accordance with JISK7236, a weight average molecular weight ($M_w$) was determined by using gel permeation chromatography (GPC) with polystyrene standards and an isomer content of a bisphenol-F is determined by using liquid chromatography with the following conditions.

Equipment: HP1090

Column: Chromato packings center Ultron N-C18-L 4.6mm×250 mm

Detector: UV 254 nm

Oven Temperature: 45° C.

Injection Volume: 10 μL

Flow Rate: 1 ml/minutes

Mobile phase: water-acetonitrile

Sample Concentration: 2 wt percent in acetonitrile

Example 1

157 parts of bisphenol-A epoxy resin (EEW:186.5 g/eq), 73.1 parts of bisphenol-F (4-hydroxyphenyl-2'-hydroxyphenylmethane content: 23.0 percent; bis(2-hydroxyphenyl)methane content: 70.0 percent; and bis(4-hydroxyphenyl)methane content: 4.0 percent) were weighed and charged into 250 mL round bottom flask equipped with a condenser, thermometer and an air-driven steel stirrer. The mixture is heated up to about 90° C. under nitrogen atmosphere. Triphenylethylphosphonium acetate (831 ppm based on solid resin content) was added to the mixture as a catalyst and temperature was raised to 190° C. At this point, the reaction exothermed and a temperature of up to about 190° C. is maintained for several minutes without external heating. The mixture is heated at about 185° C. and for about an additional 20 minutes, then cooled down to room temperature to stop reaction. A high molecular weight epoxy resin (EEW:2194, $M_w$:10874) was obtained.

Example 2

106 parts of bisphenol-A type epoxy resin (EEW:186.5 g/eq.) and 49.2 parts of bisphenol-F (4-hydroxyphenyl-2'-hydroxyphenylmethane content:65.1 percent; bis(2-hydroxyphenyl)methane content:29.8 percent; bis(4-hydroxyphenyl)methane content:3.8 percent) were reacted as the same way described in Example 1 for about 20 minutes. A high molecular weight epoxy resin (EEW:2290, $M_w$:10602) was obtained.

Example 3

157 parts of bisphenol-A type epoxy resin (EEW:186.5 g/eq.) and 73.1 parts of bisphenol-F (4-hydroxyphenyl-2'-hydroxyphenylmethane content:100 percent) were reacted in the same way described as in Example 1 for about 45 minutes. A high molecular weight epoxy resin (EEW:2380, $M_w$:10534) was obtained.

Comparative Example 1

158 parts of bisphenol-A epoxy resin (EEW:186.5 g/eq.) and 72.3 parts of bisphenol-F (bis(4-hydroxyphenyl)methane content:100 percent) were reacted as the same way described in Example 1 for about 20 minutes. A high molecular weight epoxy resin (EEW:2057, $M_w$:12189) was obtained.

Comparative Example 2

157 parts of bisphenol-A epoxy resin (EEW:186.5 g/eq.) and 73.1 parts of bisphenol-F (4-hydroxyphenyl-2'-hydroxyphenylmethane content:44.7 percent, bis(2-hydroxyphenyl)methane content:14.6 percent, bis(4-hydroxyphenyl)methane content:39.8 percent) were reacted as the same way described in the Example 1 for about 20 minutes. A high molecular weight epoxy resin (EEW:2275, $M_w$:11915) was obtained.

Comparative Example 3

157 parts of bisphenol-A type epoxy resin (EEW:186.5 g/eq.) and 73.1 parts of bisphenol-F (4-hydroxyphenyl-2'-hydroxyphenylmethane content:55.0 percent, bis(2-hydoroxyphenyl)methane content:18.0 percent, bis(4-hydroxyphenyl)methane content:26.0 percent) were reacted as the same way described in Example 1 for about 20 minutes. A high molecular weight epoxy resin (EEW:2263, $M_w$:11402) was obtained.

Example 4

90.4 parts of bisphenol-A type epoxy resin (EEW:186.5 g/eq.) and 34.6 parts of bisphenol-F (4-hydroxyphenyl-2'-hydroxyphenylmethane content:26.0 percent, bis(2-hydroxyphenyl)methane content:68.0 percent, bis(4-hydroxyphenyl)methane content:6.0 percent) were reacted as the same way described in Example 1 for about 20 minutes. A high molecular weight epoxy resin (EEW:968, $M_w$:2976) was obtained.

Comparative Example 4

126.6 parts of bisphenol-A type epoxy resin (EEW:186.5 g/eq.) and 48.4 parts of bisphenol-F (4-hydroxyphenyl-2'-hydroxyphenylmethane content:55.0 percent, bis(2-hydroxyphenyl)methane content:18.0 percent, bis(4-hydroxyphenyl)methane content:27.0 percent) were reacted as the same way described in the Example 1 for about 20 minutes. A high molecular weight epoxy resin (EEW:935, $M_w$:3027) was obtained.

A melt viscosity at 175° C. of the epoxy resins obtained by Examples 1, 2 and 3 and Comparative Examples 1, 2 and 3 were measured. The epoxy resins obtained by Example 4 and Comparative Example 4 were respectively dissolved into a 50:50 mixture solvent of methylethyl ketone and toluene as 60 percent solid resin content, and its viscosity were measured.

The high molecular weight epoxy resins obtained by Examples 1 to 4 and Comparative Example 1 to 4 were dissolved in an 80:20 mixture solvent of 2-butoxyethanol and cyclohexanone where the solutions give about Gardner G viscosity. A mixture containing 10 percent (based on solid content) of allyl ethers of mono-, di-, and trimethylol phenols (Methylon 75108 available from BTL Special Resin Co.,) and 0.75 percent (based on solid resin content) of phosphoric acid were added to the solution as hardener and catalyst respectively. The solution was applied to tin-free steel plate with wire-wound drawdown rods according to a modified ASTM D-447 to give cured coatings of 5±0.5 μm. The coated panels were cured at 205° C. for 10 minutes. The sample panels were subjected to 0T bending test, and leakage amperage was measured by potentiostat method. Flexibility of cured film is increased when this value is decreased.

Evaluation result of the epoxy resins obtained by Examples 1 to 3 and Comparative Examples 1 to 3 are summarized as shown in Tables I and II.

TABLE I

| | Example | | |
|---|---|---|---|
| | 1 | 2 | 3 |
| EEW | 2194 | 2290 | 2380 |
| $M_w$ | 10874 | 10602 | 10534 |
| Ortho Ratio *1 | 81.5 | 66.7 | 50.0 |
| A *2 | 23.0 | 73.8 | 100 |
| B *3 | 70.0 | 29.8 | 0 |
| Melt Viscosity (cps) | 5500 | 6500 | 7250 |
| Leakage Amperage (mA) | 1060 | 905 | 1133 |

TABLE II

| | Comparative Example | | |
|---|---|---|---|
| | 1 | 2 | 3 |
| EEW | 2057 | 2275 | 2263 |
| $M_w$ | 12189 | 11915 | 11402 |
| Ortho Ratio *1 | 0 | 37.0 | 45.5 |
| A *2 | 0 | 44.7 | 55.0 |
| B *3 | 0 | 14.6 | 18.0 |
| Melt Viscosity (cps) | 28,000 | 15625 | 11875 |
| Leakage Amperage (mA) | 3863 | 1658 | 1703 |

TABLE III

|  | Example 4 | Comparative Example 4 |
|---|---|---|
| EEW | 968 | 935 |
| $M_w$ | 2976 | 3027 |
| Ortho Ratio *1 | 81.0 | 45.5 |
| A (%) *2 | 26.0 | 55.0 |
| B (%) *3 | 68.0 | 18.0 |
| Solution Viscosity (cps) | 300 | 400 | wherein:
Ortho Ratio is an abbreviation of ortho hydroxyl group ratio defined as equation (1) in the specification and it represents (A+B)/2 wherein A and B are defined later; A represents a content of 4-hydroxyphenyl-2'-hydroxy-phenylmethane in bisphenol-F in weight percent; and B represents a content of bis(2-hydroxyphenyl)methane in bisphenol-F in weight percent.

As shown in Tables I and II, the epoxy resins of Examples 1, 2 and 3 which are prepared from bisphenol-F having a higher ortho hydroxyl group ratio, show lower melt viscosity compared to the epoxy resins of Comparative Examples 1, 2 and 3 having an equivalent EEW and $M_w$ which is prepared from bisphenol-F having lower ortho hydroxyl group ratio. Furthermore, as shown in Table III, the epoxy resin of Example 4 which prepared from bisphenol-F having a higher ortho hydroxyl group ratio, shows lower solution viscosity compared to the epoxy resin of Comparative Example 4, having about equivalent EEW and $M_w$, which is prepared from bisphenol-F having a lower ortho hydroxyl group ratio. Moreover, the epoxy resins prepared from bisphenol-F having a high ortho hydroxyl group ratio shows lower leakage amperage of potentiostat test, therefore, it means flexibility of the cured resin is superior to the epoxy resin prepared from bisphenol-F having lower ortho hydroxyl group ratio.

The bisphenol type epoxy resin of the present invention has improved melt viscosity and/or solution viscosity when dissolved in a solvent compared to conventional epoxy resins having a lower ortho isomer content. Furthermore, the epoxy resin of the present invention has improved physical properties such as flexibility.

We claim:

1. An epoxy or phenoxy resin comprising repeating units derived from a bisphenol F isomeric mixture, wherein at least 46 percent and no more than 95 percent of the hydroxyl groups in the bisphenol F are in the ortho position with respect to the methylene group said resin having a lower melt and solution viscosity than a resin made from a corresponding bisphenol F isomeric mixture having a lower proportion of ortho phenol moieties.

2. An epoxy or phenoxy resin of claim 1 wherein the epoxy resin is prepared by reacting a compound having at least one epoxy group and a bisphenol.

3. The epoxy or phenoxy resin of claim 2 wherein the content of the bisphenol-F is more than 10 weight percent of the prepared epoxy resin.

4. The epoxy or phenoxy resin of claim 3 wherein the compound having at least one epoxy group is an epoxy resin derived from a bisphenol.

5. The epoxy or phenoxy resin of claim 3 wherein the compound having at least one epoxy group is an epoxy resin derived from at least bisphenol A.

6. The epoxy or phenoxy resin of claim 2 wherein bisphenol F satisfies the following equation:

$$46.0 \leq (A+2B)/2 \leq [100]95$$

wherein:
A represents the content of [4-hydroxy[phenyl]1-2'-hydroxy-phenylmethane]4-hydroxyphenyl-2'-hydroxyphenylmethane in the bisphenol F; and B represents the content of bis(2-hydroxyphenyl)methane in the bisphenol F.

7. The epoxy or phenoxy resin of claim 6 wherein the epoxy resin derived from a bisphenol is derived from bisphenol A and has an epoxy equivalent weight of up to about 200.

8. The epoxy or phenoxy resin of claim 6 wherein:

$$48 \leq (A+2B)/2 \leq 95.$$

9. The epoxy or phenoxy resin of claim 6 wherein:

$$50 \leq (A+2B)/2 \leq 90.$$

10. An epoxy or phenoxy resin comprising repeating units derived from bisphenol F, wherein at least 60 percent and no more than 90 percent of the hydroxyl groups in the bisphenol F are in the ortho position with respect to the methylene group; wherein the epoxy resin is prepared by reacting a compound having at least one epoxy group and a bisphenol; and wherein bisphenol F satisfies the following equation:

$$60 \leq (A+2B)/2 \leq 90$$

wherein:
A represents the content of 4-hydroxyphenyl-2'-hydroxyphenylmethane in the bisphenol F; and B represents the content of bis(2-hydroxyphenyl)methane in the bisphenol F.

11. The epoxy or phenoxy resin of claim 1, wherein at least 48 percent of the hydroxyl groups in the bisphenol-F are in the ortho position with respect to the methylene group.

12. The epoxy or phenoxy resin of claim 11, wherein at least 50 percent of the hydroxyl groups in the bisphenol-F are in the ortho position with respect to the methylene group.

13. An epoxy or phenoxy resin comprising repeating units derived from a bisphenol F isomeric mixture, wherein at least 60 percent and no more than 95 percent of the hydroxyl groups in the bisphenol F are in the ortho position with respect to the methylene group said resin having a lower melt and solution viscosity than a resin made from a corresponding bisphenol F isomeric mixture having a lower proportion of ortho phenol moieties.

14. The epoxy or phenoxy resin of claim 11, wherein no more than about 93 percent of the hydroxyl groups in the bisphenol-F are in the ortho position with respect to the methylene group.

15. The epoxy or phenoxy resin of claim 1 which is an epoxy resin having an EEW of about 200 to about 10,000.

16. The epoxy or phenoxy resin of claim 1 which is a phenoxy resin having a weight average molecular weight of at least about 10,000.

17. The epoxy resin or phenoxy resin of claim 1 wherein no more than 90 percent of the hydroxyl groups in the bisphenol F are in the ortho position with respect to the methylene group.

18. The epoxy resin or phenoxy resin of claim 1 wherein no more than 85 percent of the hydroxyl groups in the bisphenol F are in the ortho position with respect to the methylene group.

19. The epoxy or phenoxy resin of claim 6 wherein:

$$50 \leq (A+2B)/2 \leq 85.$$

* * * * *